(12) United States Patent
Yamamoto (10) Patent No.: US 10,163,600 B2
(45) Date of Patent: Dec. 25, 2018

(54) ROTATABLE ANODE TARGET FOR X-RAY TUBE, X-RAY TUBE, AND X-RAY INSPECTION APPARATUS

(71) Applicants: Kabushiki Kaisha Toshiba, Tokyo (JP); Toshiba Materials Co., Ltd., Kanagawa (JP)

(72) Inventor: Shinichi Yamamoto, Fujisawa Kanagawa (JP)

(73) Assignees: Kabushiki Kaisha Toshiba, Tokyo (JP); Toshiba Materials Co., Ltd., Kanagawa-Ken (JP)

( * ) Notice: Subject to any disclaimer, the term of this patent is extended or adjusted under 35 U.S.C. 154(b) by 75 days.

(21) Appl. No.: 15/409,298

(22) Filed: Jan. 18, 2017

(65) Prior Publication Data
US 2017/0125199 A1  May 4, 2017

Related U.S. Application Data

(63) Continuation of application No. PCT/JP2015/003806, filed on Jul. 29, 2015.

(30) Foreign Application Priority Data

Jul. 29, 2014 (JP) .................................. 2014-154133

(51) Int. Cl.
 *H01J 35/10* (2006.01)
 *H01J 35/26* (2006.01)
 (Continued)

(52) U.S. Cl.
 CPC ............ *H01J 35/101* (2013.01); *H01J 35/10* (2013.01); *H01J 35/105* (2013.01); *H01J 35/26* (2013.01);
 (Continued)

(58) Field of Classification Search
 CPC ......... H01J 2235/102; H01J 2235/1086; H01J 2235/1204; H01J 35/101; H01J 35/105; H01J 35/26; H01J 2235/081; H01J 35/10
 See application file for complete search history.

(56) References Cited

U.S. PATENT DOCUMENTS 6,487,275 B1 * 11/2002 Baba ....................... H01J 35/10
                                                    378/143
6,707,883 B1 *  3/2004 Tiearney, Jr. ......... H01J 35/108
                                                    378/143
(Continued)

FOREIGN PATENT DOCUMENTS

CN       101326297 A    12/2008
CN       102473572 A     5/2012
(Continued)

OTHER PUBLICATIONS

Extended European Search Report dated Feb. 13, 2018 in corresponding application No. EP 15828014.9.

*Primary Examiner* — Chih-Cheng Kao
(74) *Attorney, Agent, or Firm* — Harness, Dickey & Pierce, PLC (57) ABSTRACT

A rotatable anode target for an X-ray tube (1) of the present invention includes a metallic disc (2) which includes a first crystal structure; a metallic cylinder (3) which is joined with the metallic disc and includes a second crystal structure, where a first average aspect ratio of first crystal grains positioning at a first region within 2 mm from an interface between the metallic disc and the metallic cylinder is less than 2, and a second average aspect ratio of second crystal grains positioning at a second region within 2 mm from the interface is 2 or more and 8 or less. It is thereby possible to provide an X-ray tube target which has high heat release performance and where thermal deformation is difficult to occur.

15 Claims, 3 Drawing Sheets

(51) Int. Cl.
   *A61B 6/03*          (2006.01)
   *G01N 23/046*     (2018.01)
   *A61B 6/00*          (2006.01)

(52) U.S. Cl.
   CPC ................ *A61B 6/03* (2013.01); *A61B 6/032* (2013.01); *A61B 6/40* (2013.01); *A61B 6/4488* (2013.01); *G01N 23/046* (2013.01); *H01J 2235/081* (2013.01); *H01J 2235/102* (2013.01); *H01J 2235/1086* (2013.01); *H01J 2235/1204* (2013.01)

(56) References Cited

U.S. PATENT DOCUMENTS

| | | | |
|---|---|---|---|
| 2009/0290685 A1* | 11/2009 | Aoyama | ................ H01J 35/08 378/144 |
| 2012/0099703 A1 | 4/2012 | Kraft et al. | |
| 2012/0163549 A1 | 6/2012 | Hove et al. | |

FOREIGN PATENT DOCUMENTS

| | | | |
|---|---|---|---|
| CN | 102834894 A | | 12/2012 |
| EP | 1953254 A1 | | 8/2008 |
| JP | H0574392 A | | 3/1993 |
| JP | 2003068239 A | | 3/2003 |
| JP | 2010212088 A | | 9/2010 |
| JP | 2012532409 A | | 12/2012 |
| JP | 2013502034 A | | 1/2013 |
| JP | 5238259 B2 | | 7/2013 |
| WO | WO2007/049761 A1 | | 5/2007 |
| WO | WO2011/001343 A1 | | 1/2011 |
| WO | WO2011/018750 A1 | | 2/2011 |

\* cited by examiner

ROTATABLE ANODE TARGET FOR X-RAY TUBE, X-RAY TUBE, AND X-RAY INSPECTION APPARATUS

CROSS-REFERENCE TO RELATED APPLICATIONS

This application is a continuation of prior International Application No. PCT/JP2015/003806 filed on Jul. 29, 2015, which is based upon and claims the benefit of priority from Japanese Patent Application No. 2014-154133 filed on Jul. 29, 2014; the entire contents of all of which are incorporated herein by reference.

FIELD

Embodiments described herein relate generally to a rotatable anode target for an X-ray tube, an X-ray tube, and an X-ray inspection apparatus.

BACKGROUND

An X-ray tube is mounted on various X-ray inspection apparatuses such as a CT (computed tomography) device. The X-ray tube includes a rotatable anode target for an X-ray tube. The rotatable anode target includes a disc-shaped member including an X-ray irradiator, and a rotation shaft integrated with the disc-shaped member. A rotatable anode target radiates an X-ray by an electron beam emitted from a cathode irradiated on the X-ray irradiator. When the X-ray radiation is repeated, a temperature at the X-ray irradiator increases. The rotatable anode target is easy to be thermally deformed under a high-temperature.

A rotation structure of the rotatable anode target is divided into two kinds of structures of a ball bearing structure using a bearing ball and a dynamic pressure bearing structure. The ball bearing structure is a structure where the rotation shaft is rotated while being supported by the bearing ball. The dynamic pressure bearing structure is a structure including: a cylinder of a rotation shaft having a cylindrical shape; a fixed shaft provided in the cylinder and having a spiral shape or the like; and a sliding bearing having a liquid-metal lubricant such as a liquid metal filled in the cylinder.

The ball bearing structure is a structure including the bearing ball, and therefore, it is possible to obtain a stable high-speed rotation. However, there has been a problem that an operation sound is loud because the rotation shaft is in contact with the bearing ball.

The dynamic pressure bearing structure is a structure including the sliding bearing. Accordingly, the operation sound and vibration are very small. Besides, abrasion is also small, and therefore, operating life thereof is long. The dynamic pressure bearing structure uses the liquid-metal lubricant such as the liquid metal, and therefore, it is excellent in heat release performance at the disc-shaped member including the X-ray irradiator.

DETAILED DESCRIPTION

A rotatable anode target for an X-ray tube according to the embodiment includes: a metallic disc which includes a first crystal structure containing a plurality of first crystal grains; a metallic cylinder which is joined with the metallic disc and includes a second crystal structure containing a plurality of second crystal grains; and an X-ray irradiator which is provided at a surface of the metallic disc. A first average aspect ratio of the first crystal grains positioning at a first region within 2 mm from an interface between the metallic disc and the metallic cylinder is less than 2. A second average aspect ratio of the second crystal grains positioning at a second region within 2 mm from the interface is 2 or more and 8 or less.

Figure 1:
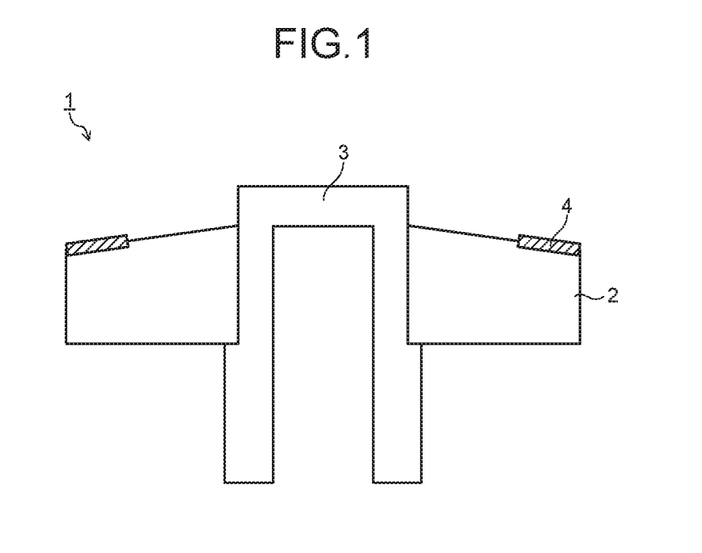
FIG. 1 is a sectional schematic view illustrating an example of a rotatable anode target for an X-ray tube.

FIG. 1 is a sectional view illustrating an example of a rotatable anode target for an X-ray tube. A rotatable anode target for an X-ray tube 1 illustrated in FIG. 1 includes a metallic disc 2, a metallic cylinder 3, and an X-ray irradiator 4.

The metallic disc 2 includes a hole to be connected to the metallic cylinder 3. A diameter of the metallic disc 2 is preferably, for example, 100 mm or more and 200 mm or less. A thickness of the metallic disc is preferably, for example, 10 mm or more and 60 mm or less. A diameter of the hole to be connected to the metallic cylinder 3 is preferably, for example, 30 mm or more and 70 mm or less.

The metallic disc 2 preferably contains at least one metal from among molybdenum, tungsten, tantalum, niobium, and iron, or an alloy whose major component is the above-stated metal. When an X-ray is irradiated from the rotatable anode target for an X-ray tube, the rotatable anode target becomes high-temperature. Accordingly, heat resistance of the metallic disc 2 is preferably high. For example, metals such as molybdenum (melting point of 2620° C.), tungsten (melting point of 3400° C.), tantalum (melting point of 2990° C.), or niobium (melting point of 2470° C.) each have a high melting point, and therefore, they are preferable as a material of the metallic disc 2. Further, molybdenum or a molybdenum alloy is easy to be processed and has low price among high melting point metals, and therefore, they are more preferable as the material of the metallic disc 2.

In case of the alloy, an alloy containing at least one metallic compound between a metal oxide and a metal carbide may be used as the metallic disc 2. When an oxide or a carbide is contained, the metallic disc 2 preferably contains at least one material of the oxide and the carbide of Ti (titanium), Zr (zirconium), Hf (hafnium), or a rare-earth element for 0.1 mass % or more and 5 mass % or less. As the rare-earth element, there can be cited, for example, La (lanthanum), Ce (cerium). The metal oxide and the metal carbide have effects such as strength improvement of the high melting point metal, suppression of gas generation under high-temperature. Besides, the metal oxide and the metal carbide also have an effect of suppressing a grain growth of crystal grains of the high melting point metal.

When iron is used, it is preferable to use an alloy tool steel. The alloy tool steel is formed by adding molybdenum, tungsten, chromium, silicon, vanadium, nickel, and so on to a carbon tool steel. For example, an alloy tool steel for mold (for example, a steel kogu dice: SKD) is preferably used as the alloy tool steel.

The metallic cylinder 3 is one member constituting a rotatable anode target for an X-ray tube having a dynamic pressure bearing structure, and has a function as a rotation shaft of an X-ray tube. The metallic cylinder 3 has a cylindrical shape. The metallic cylinder 3 is joined with the metallic disc 2. In FIG. 1, a side surface of the metallic cylinder 3 is joined with a side surface of the hole of the metallic disc 2. A state where the metallic cylinder 3 is joined with the metallic disc 2 is also called as a state where the metallic cylinder 3 is integrated with the metallic disc 2. Namely, the rotatable anode target for an X-ray tube 1 illustrated in FIG. 1 includes the integrated metallic disc 2 and metallic cylinder 3.

A diameter of the metallic cylinder 3 is preferably, for example, 40 mm or more and 80 mm or less. The metallic cylinder 3 preferably contains at least one metal from among molybdenum, tungsten, tantalum, niobium, and iron, or an alloy whose major component is the above-stated metal.

The metallic cylinder 3 may contain the metal oxide and the metal carbide. When iron is used, the metallic cylinder 3 is preferably the alloy tool steel, further the alloy tool steel for mold. A material of the metallic cylinder 3 may be the same as the metallic disc 2. The material of the metallic cylinder 3 may be a material different from the metallic disc 2.

The X-ray irradiator 4 is provided at the metallic disc 2. The X-ray irradiator 4 is provided at an upper surface of the metallic disc 2. The X-ray irradiator 4 is an area generating the X-ray by an electron beam irradiated from a cathode. The X-ray irradiator 4 preferably contains, for example, a Re—W alloy.

Figure 2:
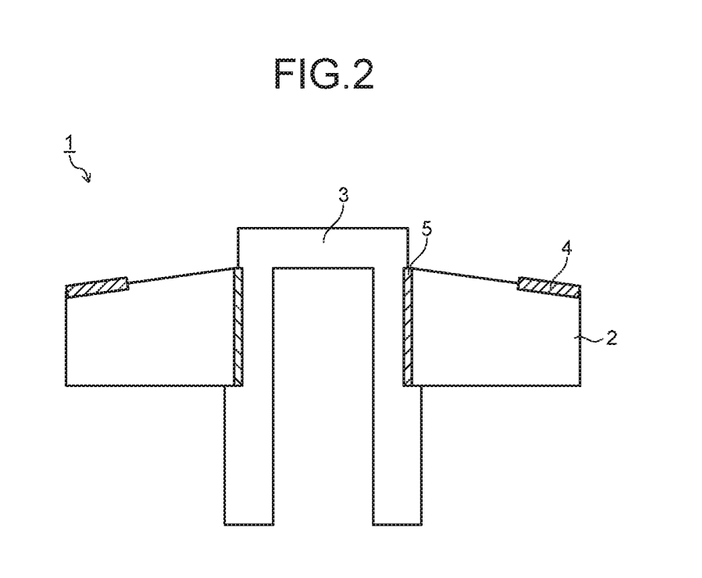
FIG. 2 is a sectional schematic view illustrating another example of the rotatable anode target for an X-ray tube.

FIG. 2 is a sectional view illustrating another example of the rotatable anode target for an X-ray tube. The rotatable anode target 1 illustrated in FIG. 2 includes the metallic disc 2, the metallic cylinder 3, the X-ray irradiator 4, and a brazing material layer 5. The metallic cylinder 3 is joined with the metallic disc 2 by the brazing material layer 5 therebetween. The description of FIG. 1 can be appropriately cited as a description of a common part with the rotatable anode target 1 illustrated in FIG. 1.

The brazing material layer 5 is provided between the metallic disc 2 and the metallic cylinder 3. A melting point of a brazing material used for the brazing material layer 5 is preferably 1500° C. or more. When an X-ray inspection apparatus is continuously operated, a temperature of the rotatable anode target increases up to around 1000° C. When the melting point of the brazing material is less than 1500° C., reliability of the joint between the metallic disc 2 and the metallic cylinder 3 is easy to be lowered.

The brazing material whose melting point is 1500° C. or more contains, for example, at least one element from among Ti, Zr, Hf, Pt, Co, Cr, Ni, and V as a major component. The brazing material whose melting point is 1500° C. or more further preferably contains, for example, at least one element from among Ti, Zr, Hf, and Pt as the major component. The brazing material whose melting point is 1500° C. or more further preferably contains at least one element between Ti and Zr as the major component. The brazing material whose major component is at least one element between Ti and Zr is used, and thereby, it is possible to increase a joint strength between the brazing material layer 5 and molybdenum (molybdenum alloy).

Figure 3:
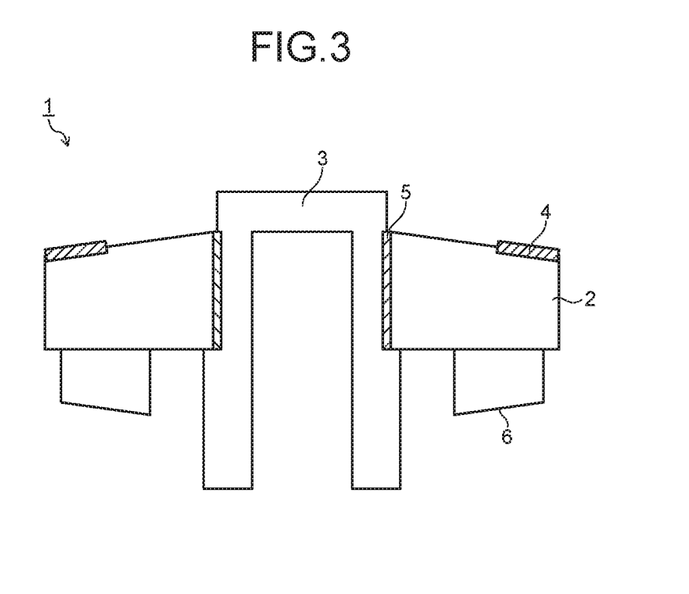
FIG. 3 is a sectional schematic view illustrating still another example of the rotatable anode target for an X-ray tube.

FIG. 3 is a sectional view illustrating still another example of the rotatable anode target for an X-ray tube. The rotatable anode target 1 illustrated in FIG. 3 includes the metallic disc 2, the metallic cylinder 3, the X-ray irradiator 4, the brazing material layer 5, and a graphite member 6. The description of FIG. 1 can be appropriately cited as a description of a common part with the rotatable anode target 1 illustrated in FIG. 1.

The graphite member 6 is joined with the metallic disc 2. In FIG. 3, the graphite member 6 is joined with a lower surface of the metallic disc 2. The graphite member 6 is provided, and thereby, it is possible to easily release heat of the metallic disc 2. Besides, a thickness of the metallic disc 2 can be reduced, and it becomes possible to reduce a weight of the rotatable anode target 1.

For example, a metal oxide coating film may be provided at least at a part of an outer periphery of the metallic disc 2 without being limited to structures illustrated in FIG. 1 to FIG. 3. For example, the metal oxide coating film may be provided at a region of the metallic disc 2 where the X-ray irradiator 4 is not provided. The metal oxide coating film preferably contains, for example, an alloy of a titanium oxide ($TiO_2$) and an aluminum oxide ($Al_2O_3$). Conformability between $TiO_2$, $Al_2O_3$ and at least one metal from among molybdenum, tungsten, tantalum, niobium, and iron or the alloy whose major component is the above-stated metal which is applied for the metallic disc 2 is good. It is therefore possible to form a film with high adhesiveness. The metal oxide coating film is provided, and thereby, it is possible to accelerate heat radiation of the rotatable anode target 1, and to decrease the temperature.

As a formation method of the metal oxide coating film, there can be cited, for example, film-forming technologies such as a thermal spraying method, a sputtering method, and coating technologies such as coating and burning of paste. A film thickness of the metal oxide coating film is preferably 300 μm or less. When it exceeds 300 μm, not only an effect as stated above or the like cannot be obtained but also there is a possibility that the heat release performance is lowered.

Figure 4:
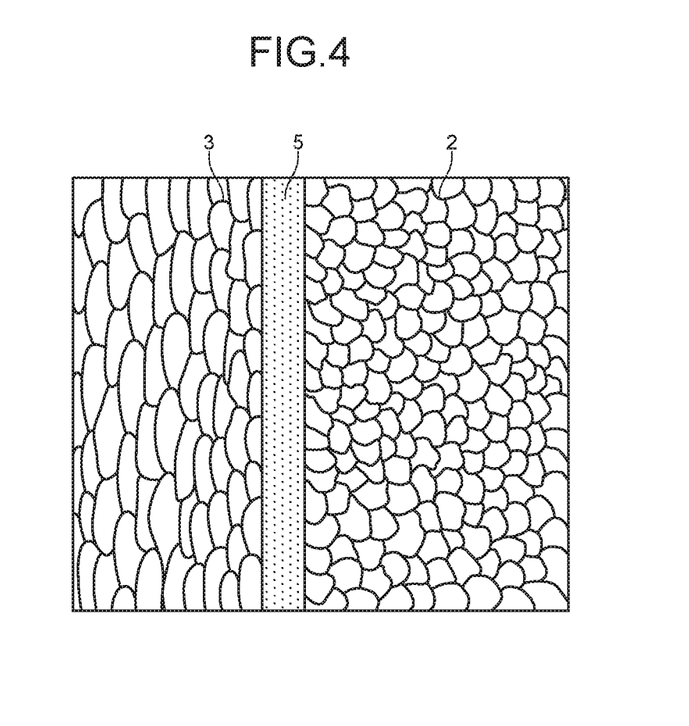
FIG. 4 is a sectional schematic view illustrating an example of a cross section of the rotatable anode target for an X-ray tube including an interface between a metallic disc and a metallic cylinder.

FIG. 4 is a sectional schematic view of the rotatable anode target 1 in a direction perpendicular to a length direction of the metallic cylinder 3 including an interface between the metallic disc 2 and the metallic cylinder 3. The metallic disc 2 has a first crystal structure having a plurality of first crystal grains. The metallic cylinder 3 has a second crystal structure having a plurality of second crystal grains.

An average aspect ratio of the plurality of first crystal grains is less than 2, more preferably 1.6 or less. An average aspect ratio of the plurality of second crystal grains is 2 or more, more preferably 2.5 or more. An upper limit of the average aspect ratio is preferably 8 or less. When the average aspect ratio exceeds 8, a load of work becomes large. Besides, there is a possibility that working strain remains in the metallic cylinder.

An aspect ratio of the crystal grains is found as, for example, described below. The cross-section of the rotatable anode target 1 in the direction perpendicular to the length direction of the metallic cylinder 3 including the interface between the metallic disc 2 and the metallic cylinder 3 is photographed by a scanning electron microscope (SEM). A maximum diameter of individual crystal grains taken in a macrophotograph of the photographed cross section is defined as a long axis. A grain size passing on a center of the long axis and in a direction perpendicular to the long axis direction on the macrophotograph is defined as a short axis. A ratio of the long axis relative to the short axis corresponds to the aspect ratio of the crystal grain. The above-stated operation is performed for 100 pieces of first crystal grains in the first crystal structure of the metallic disc 2, and an average value of the obtained plurality of aspect ratios is defined as a first average aspect ratio. Besides, the above-stated operation is performed for each of 100 pieces of second crystal grains in the second crystal structure of the metallic cylinder 3, and an average value of the obtained plurality of aspect ratios is defined as a second average aspect ratio. In this case, measurement objects of the aspect ratio are the first crystal grains positioning in a first region within 2 mm from the interface between the metallic disc 2 and the metallic cylinder 3, and the second crystal grains positioning in a second region within 2 mm from the interface. In case of FIG. 4, the crystal grains positioning in a region within 2 mm from the brazing material layer 5 are also set as the measurement objects.

When the aspect ratio is less than 2, the crystal grain has a substantial spherical structure. In the spherical structure, a propagation way of heat does not change depending on directions. Accordingly, the average aspect ratio of the first crystal grains is adjusted to be less than 2, and thereby, it is possible to release the heat from a whole surface of the metallic disc 2. For example, when the electron beam is irradiated on the X-ray irradiator 4, a temperature of the X-ray irradiator 4 is very high to be approximately 2500° C. It is therefore possible to release the heat from the whole surface of the metallic disc 2 by using the metallic disc 2 including the first crystal structure containing the first crystal grains whose average aspect ratio is less than 2.

When the aspect ratio is 2 or more, the crystal grain has a substantial columnar structure. In the columnar structure, the heat is easy to be propagated in a long axis direction than a short axis direction of the crystal grain. Accordingly, the average aspect ratio of the second crystal grains is adjusted to be 2 or more, and the long axis direction of the second crystal grains is substantially aligned in the length direction of the metallic cylinder 3, and thereby, it is possible to easily release the heat at the metallic disc 2 along the length direction of the metallic cylinder 3. Accordingly, the heat release performance of the rotatable anode target as a whole improves, and the thermal deformation due to thermal expansion can be made small. For example, in case of the rotatable anode target having the dynamic pressure bearing structure, an inner surface of the metallic cylinder 3 is in contact with the liquid-metal lubricant, and therefore, it is possible to efficiently release the heat.

Figure 5:
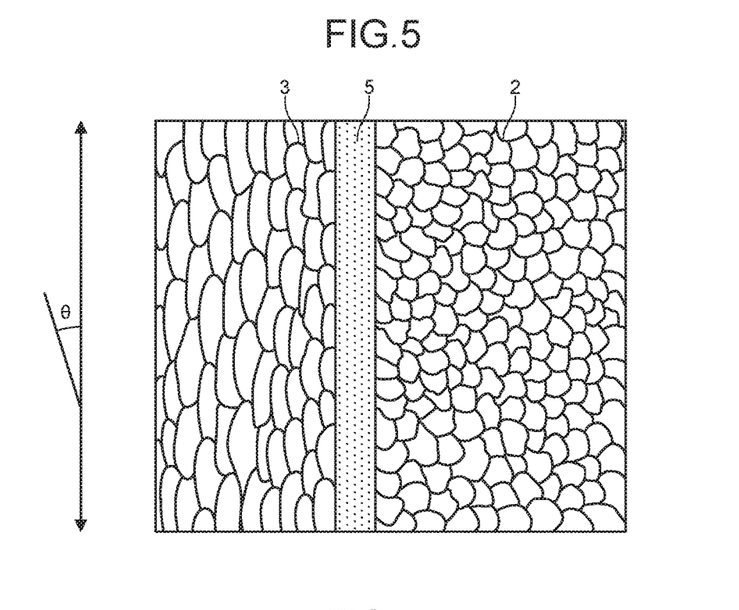
FIG. 5 is a sectional schematic view illustrating an example of the cross section of the rotatable anode target for an X-ray tube including the interface between the metallic disc and the metallic cylinder.

A state where the long axis direction of the second crystal grains is substantially aligned with the length direction of the metallic cylinder 3 is defined as described below. FIG. 5 is a sectional schematic view of the rotatable anode target 1 in a direction perpendicular to the length direction of the metallic cylinder 3 including the interface between the metallic disc 2 and the metallic cylinder 3. The cross-section of the rotatable anode target 1 in the direction perpendicular to the length direction of the metallic cylinder 3 including the interface between the metallic disc 2 and the metallic cylinder 3 is photographed by the scanning electron microscope (SEM). A first line indicating the long axis (maximum diameter) of the individual second crystal grains taken in a macrophotograph (SEM photograph) of the photographed cross section is drawn. A second line indicating the length direction of the metallic cylinder 3 is drawn (a left side in FIG. 5). A deviation between the first line and the second line is set as θ. The state where the long axis direction of the second crystal grains is substantially aligned with the length direction of the metallic cylinder 3 is a state where θ is −25 degrees or more and +25 degrees or less.

Among the second crystal grains whose average aspect ratio is 2 or more, the deviation between the long axis direction of the second crystal grains whose number ratio per a unit area of 1000 μm×1000 μm is 80% or more and 100% or less and the length direction of the metallic cylinder 3 is preferably −25 degrees or more and +25 degrees or less.

An average grain size of the first crystal grains is preferably 20 μm or more and 500 μm or less. When the average grain size is less than 20 μm, a ratio of grain boundaries is large. When there are a lot of grain boundaries, there is a possibility that the heat is difficult to be propagated, and the heat release performance is lowered. When the average grain size exceeds 500 μm, there is a possibility that the thermal deformation due to the thermal expansion of the first crystal grains becomes large. The average grain size of the first crystal grains is more preferably 50 μm or more and 200 μm or less.

An average grain size of the second crystal grains is preferably 20 μm or more and 800 μm or less. When the average grain size is less than 20 μm, a ratio of grain boundaries becomes large. When there are a lot of grain boundaries, there is a possibility that the heat is difficult to be propagated, and the heat release performance is lowered. When the average grain size exceeds 800 μm, there is a possibility that the thermal deformation due to the thermal expansion of the second crystal grains becomes large. The average grain size of the second crystal grains is more preferably 50 μm or more and 500 μm or less.

The average grain size is found as described below. Information of the long axis and the short axis of the crystal grains used for measurement of the aspect ratio is used, and there is set such that (long axis+short axis)÷2=crystal grain size. The above-stated operation is performed for 100 pieces of first crystal grains, and an average value is set as the average grain size of the first crystal grains. Besides, the above-stated operation is performed for 100 pieces of second crystal grains, and an average value is set as the average grain size of the second crystal grains.

The rotatable anode target of the embodiment is excellent in the heat release performance and the heat resistance, and therefore, the thermal deformation is difficult to occur. It is therefore possible to make operating life of the rotatable anode target long. Further, reliability of an X-ray tube and an X-ray inspection apparatus using the rotatable anode target for target according to the embodiment is high.

As a rotation drive structure of the rotatable anode target, the dynamic pressure bearing structure or a ball bearing structure can be applied. The rotatable anode target of the embodiment includes the metallic cylinder. Accordingly, it is suitable for the dynamic pressure bearing structure.

Figure 6:
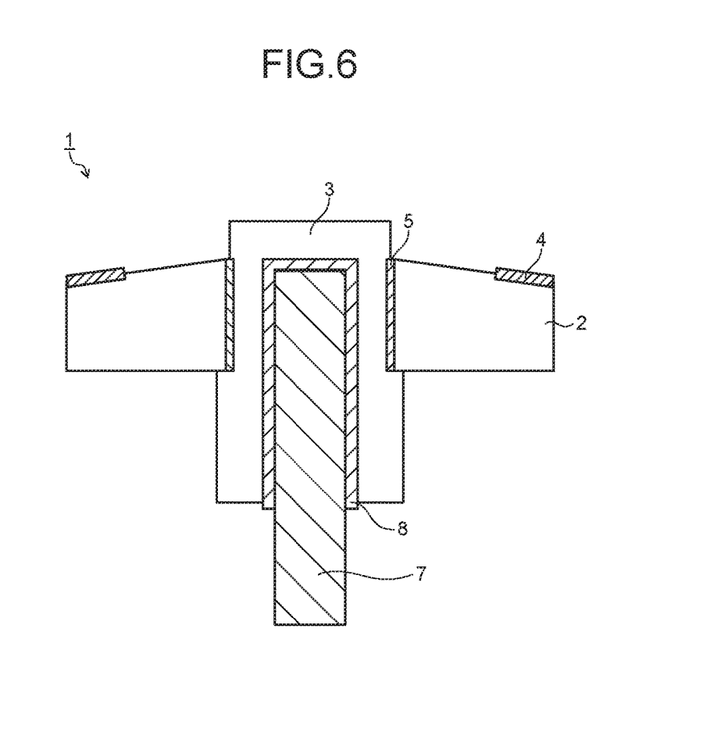
FIG. 6 is a sectional schematic view illustrating an example of a rotatable anode target for an X-ray tube having a dynamic pressure bearing structure.

FIG. 6 is a sectional schematic view illustrating an example of the rotatable anode target having the dynamic pressure bearing structure. The rotatable anode target 1 illustrated in FIG. 6 includes the metallic disc 2, the metallic cylinder 3, a fixed shaft 7, and a liquid-metal lubricant 8. The description of FIG. 1 can be appropriately cited as a description of a common part with the rotatable anode target 1 illustrated in FIG. 1.

A surface of the fixed shaft 7 and an inner surface of the metallic cylinder 3 may each have a spiral groove in a radial direction or a thrust direction. A lower direction in the drawing of the metallic cylinder 3 is sealed with a not-illustrated thrust ring or the like. A stator or the like to enable rotation drive by a rotating magnetic field is provided. In case of the X-ray tube, it may be combined with the cathode irradiating the electron beam on the X-ray irradiator 4 and a vacuum vessel holding the rotatable anode target 1 and the cathode, and so on.

The liquid-metal lubricant 8 is supplied between the metallic cylinder 3 and the fixed shaft 7. The liquid-metal lubricant 8 contains, for example, gallium, a gallium alloy, and so on. In the dynamic pressure bearing structure, the fixed shaft 7 is not directly in contact with the inner surface of the metallic cylinder 3, and therefore, vibration is small, and an operation sound is small. Besides, they are not directly in contact, and therefore, abrasion between the inner surface of the metallic cylinder 3 and the fixed shaft 7 seldom occurs. Accordingly, an operating life as a bearing can be made long.

The heat release performance of the rotatable anode target of the embodiment is high. The thermal deformation is therefore difficult to occur. Accordingly, it is possible to prevent that the fixed shaft 7 is directly in contact with the inner surface of the metallic cylinder 3 due to the thermal deformation at a continuous operation time. It is thereby possible to provide the X-ray tube and the X-ray inspection apparatus each having excellent long-term reliability.

The X-ray inspection apparatus is used in various fields such as a medical inspection apparatus and an industrial inspection apparatus. As the medical inspection apparatus, there can be cited a CT device (computed tomography, or the like). According to the CT device, the X-ray is irradiated on a subject (patient), transmitted X-ray is detected by a detector including a scintillator or the like to obtain an image. In recent years, it is also possible to obtain not only a two-dimensional image but also a three-dimensional image.

During the CT device is used, the temperature of the rotatable anode target increases. When the temperature of the rotatable anode target exceeds a certain temperature, it is necessary to cool the rotatable anode target by stopping measurement for a certain period of time. When the rotatable anode target is cooled, the measurement of the subject cannot be performed. The heat release performance and the thermal deformation of the rotatable anode target of the embodiment are excellent. It is therefore possible to correspond to the continuous operation of the X-ray inspection apparatus. Accordingly, the continuous operation time can be made long, and the measurement of the subject can be continuously performed for a long period of time.

Next, a manufacturing method example of the rotatable anode target of the embodiment is described. The manufacturing method is not particularly limited as long as the above-stated constitution is included, but there is the following method as a method to effectively obtain the above.

As a formation method of the metallic disc 2, there can be cited, for example, any one of a powder molding method, a hot pressing method, spark plasma sintering, and a thermal spraying method.

In the powder molding method, a raw material powder is filled in a mold to be molded. An obtained compact is degreased according to need, and thereafter, sintered. In the hot pressing method, the raw material powder is filled in the mold, and is sintered while applying a pressure and a temperature. In the spark plasma sintering, the compact is electrically sintered. In the thermal spraying method, the raw material powder is thermally sprayed to be deposited.

An atmosphere of the sintering process is preferably a vacuum atmosphere ($10^{-3}$ Pa or less) and an inert gas atmosphere. There is a possibility that a sintered compact is oxidized in an oxygen-containing atmosphere such as the air. After the sintering or the thermal spraying is performed, HIP (hot isostatic pressing) may be performed. In the HIP, it is preferable that a temperature is 1600° C. or more and 2000° C. or less, and a pressure is 100 MPa or more.

The raw material powder preferably contains one material selected from molybdenum, tungsten, tantalum, niobium, iron, or an alloy whose major component is the above-stated metal. The major component of the alloy means an alloy where the component is contained for 50 mass % or more. The metal oxide or the metal carbide may be added to the alloy.

An average grain size of the raw material powder is preferably, for example, 0.5 µm or more and 20 µm or less, further preferably 1 µm or more and 10 µm or less. The raw material powder in the above-stated range is used, and thereby, it is easy to control the average grain size of the first crystal grains to be, for example, 20 µm or more and 500 µm or less.

A compact may be formed before sintering. A molding process may include molding by a mold, CIP (cold isostatic pressing), and so on. A molding pressure is preferably 100 MPa or more and 300 MPa or less. A hole to joint the metallic cylinder 3 may be provided at the compact.

When molybdenum, tungsten, tantalum, niobium, or the alloy thereof is used as the raw material powder, a sintering temperature is preferably 1800° C. or more and 2500° C. or less. When the sintering temperature is less than 1800° C., a density of a sintered compact is easy to become low. When the sintering temperature exceeds 2500° C., there is a possibility that the grains grow too much. When iron or an iron alloy is used as the raw material powder, the sintering temperature is preferably 1000° C. or more and 1600° C. or less. A sintering atmosphere is preferably the vacuum atmosphere ($10^{-3}$ Pa or less) and the inert gas atmosphere.

Forging or machining may be performed for the sintered compact. The forging or the machining is performed, and thereby, it is possible to process the sintered compact into a desired shape of the rotatable anode target. The forging is performed, and thereby, it is possible to crush pores existing in the sintered compact. As a result, it is possible to obtain the high density metallic disc 2 whose porosity is 0% or more and 0.5% or less.

The forging preferably includes hot forging where a temperature is 1400° C. or more and 1700° C. or less, and a working ratio is 10% or more and 60% or less. When the temperature is less than 1400° C., cracks are easy to occur at the sintered compact. When the temperature exceeds 1700° C., there is a possibility that thermal deformation occurs more than necessary. The temperature of the hot forging is more preferably 1500° C. or more and 1600° C. or less. When the working ratio is less than 10%, a working amount is small, and therefore, there is a possibility that the pores are not crushed. When the working ratio exceeds 60%, the average aspect ratio of the first crystal grains is difficult to be less than 2. The working ratio is more preferably 20% or more and 50% or less. As the machining, there can be cited, for example, surface polishing or the like. At the metallic disc 2, a surface which is joined with the metallic cylinder 3 is preferably a flat surface by the polishing, or the like.

As a formation method of the X-ray irradiator 4, there can be cited a method in which a Re—W alloy powder layer is provided at a predetermined position of a compact of the metallic disc 2, and the sintering process is performed. After the sintered compact to be the metallic disc 2 is prepared, the Re—W alloy powder layer is formed to be burned. As a formation method of the Re—W alloy layer, the thermal spraying method, a CVD method, and so on may be used.

A manufacturing method of the metallic cylinder 3 is described. A sintered ingot or a melted ingot made up of a material constituting the metallic cylinder 3 is prepared. Rolling and forging are performed for these ingots to be processed to a plate-state member. It is preferable to prepare the sintered ingot at the sintering temperature of 1800° C. or more and 2500° C. or less. The atmosphere of the sintering process is the vacuum atmosphere ($10^{-3}$ Pa or less) and the inert gas atmosphere.

The plate-state member is processed into a tubular shape to thereby manufacture the metallic cylinder 3. At this time, a working ratio in a length direction of the metallic cylinder 3 is preferably 10% or more and 90% or less. The working ratio is set to 10% or more, and thereby, it becomes easy to adjust the average aspect ratio of the second crystal grains of the metallic cylinder 3 to be 2 or more. The working ratio in the length direction of the metallic cylinder 3 is set to 10% or more, and thereby, it becomes easy to align the long axis of the second crystal grains with the length direction of the metallic cylinder 3. When the working ratio exceeds 90%, it is difficult to process the plate-state member into a uniform thickness. The working ratio in the length direction of the metallic cylinder 3 is preferably 15% or more and 70% or less. When the plate-state member is processed into the tubular shape, it is preferable to determine the working ratio in consideration of the aspect ratio of crystal grains of the plate-state member. A lid member may be attached to each of a tip part and a bottom part of the metallic cylinder 3.

A raw material powder of the metallic cylinder 3 preferably contains at least one metal from among molybdenum, tungsten, tantalum, niobium, and iron, or the alloy whose major component is the above-stated metal. An average grain size of the raw material powder is preferably, for example, 0.5 µm or more and 20 µm or less, further preferably 1 µm or more and 10 µm or less. The raw material powder in this range is used, and thereby, it becomes easy to control the average grain size of the second crystal grains in the range of 20 µm or more and 800 µm or less. Besides, a strain relief heat treatment may be performed. At the metallic cylinder 3, a surface which is joined with the metallic disc 2 is preferably a flat surface by the polishing or the like.

An integration process (joining process) between the metallic disc 2 and the metallic cylinder 3 is described. As a joining method between the metallic disc 2 and the metallic cylinder 3, there can be cited, for example, a brazing method, a shrinkage fit method, a cold fit method, a pressure process, a welding process, and so on. The joining method between the metallic disc 2 and the metallic cylinder 3 is more preferably the brazing method.

In the brazing method, a brazing material is coated on joint surfaces of one of or both of the metallic disc 2 and the metallic cylinder 3. After the brazing material is coated, the metallic disc 2 and the metallic cylinder 3 are fitted. After that, they are heat-treated to be integrated.

In the brazing method, the brazing material layer 5 is formed so as to embed a space between the metallic disc 2 and the metallic cylinder 3 by melting the brazing material by the heat-treatment. For example, paste is used, and thereby, the brazing material gets in the space between the metallic disc 2 and the metallic cylinder 3. Accordingly, it is possible to firmly join the metallic disc 2 and the metallic cylinder 3. Besides, pores are difficult to be formed at the space between the metallic disc 2 and the metallic cylinder 3 because the brazing material gets in the space. It is therefore possible to improve the heat release performance between the metallic disc 2 and the metallic cylinder 3.

The shrinkage fit method is a method where the metallic disc 2 and the metallic cylinder 3 are fitted while performing the heat treatment. In the shrinkage fit method, for example, a recessed part is formed at a first member, a protruding part is formed at a second member, and the protruding part and the recessed part are fitted. The shrinkage fit method is used, and thereby, it becomes unnecessary to use the brazing material, and therefore, the process can be simplified.

The cold fit method is a method where the metallic disc 2 and the metallic cylinder 3 are fitted without performing the heat treatment. The metallic disc 2 and the metallic cylinder 3 may be fitted while cooling. The metallic disc 2 and the metallic cylinder 3 are fitted in a room temperature or while cooling, and thereby, it is possible to suppress joint failure between the metallic disc 2 and the metallic cylinder 3 due to thermal expansion. The pressure process is a method to fit the metallic disc 2 and the metallic cylinder 3 by applying pressure.

EXAMPLE

Examples 1A to 6A, Comparative Example 1A

A molybdenum (Mo) powder whose average grain size was 5 µm was prepared as the raw material powder constituting the metallic disc. The Mo powder was molded by a mold, and a disc-shaped compact having a hole to be joined with the metallic cylinder was prepared. Next, the sintering process was performed at 2000° C. in vacuum ($10^{-3}$ Pa or less). Then the forging was performed for the obtained Mo sintered compact at the working ratio illustrated in Table 1. The above-stated working ratio was the working ratio in a thickness direction of the metallic disc. The surface polishing was performed for the obtained Mo forged compact. The X-ray irradiator made up of the Re—W alloy layer was provided at an upper surface of the metallic disc. A $TiO_2$—$Al_2O_3$ film (film thickness of 40 µm) was provided at the upper surface of the metallic disc where the X-ray irradiator was not provided. The metallic disc with the diameter of 140 mm and thickness of 50 mm, having the hole to join the metallic cylinder with the diameter of 50 mm was thereby manufactured.

The molybdenum (Mo) powder whose average grain size was 5 µm was prepared as the raw material powder constituting the metallic cylinder. Next, the sintering process was performed at 2000° C. in vacuum ($10^{-3}$ Pa or less). Then the rolling and the forging were performed for the obtained Mo sintered compact at the working ratio illustrated in Table 1 to prepare the plate-state member. The above-stated working ratio was the working ratio in the length direction of the metallic cylinder 3. As stated above, the metallic cylinder whose diameter (outside diameter) was 50 mm, inside diameter was 30 mm (sheet thickness of 5 mm), and length was 100 mm was prepared.

TABLE 1

|  | Metallic Disc Working Ratio (%) | Metallic Cylinder Working Ratio (%) |
|---|---|---|
| Example 1A | 20 | 15 |
| Example 2A | 30 | 20 |
| Example 3A | 40 | 30 |

TABLE 1-continued

|  | Metallic Disc Working Ratio (%) | Metallic Cylinder Working Ratio (%) |
|---|---|---|
| Example 4A | 50 | 40 |
| Example 5A | 44 | 50 |
| Example 6A | 47 | 70 |
| Comparative Example 1A | 100 | 5 |

Next, the joining process between the metallic disc and the metallic cylinder was performed. In the joining process, the surface polishing was performed for the surface of the metallic disc to be joined with the metallic cylinder and the surface of the metallic cylinder to be joined with the metallic disc with a surface roughness of Ra 3 µm or less. Next, a Ti brazing material (melting point of 1600° C.) was prepared to be coated on each of the joint surface of the metallic disc and the joint surface of the metallic cylinder. After the metallic disc and the metallic cylinder were fitted, they were heated to 1700° C. to be joined. Rotatable anode targets according to the example 1A to the example 6A and the comparative example 1A were manufactured by the above-stated processes.

A sectional structure of the rotatable anode target including a region within 2 mm from the interface between the metallic disc and the metallic cylinder of each of the rotatable anode targets according to the examples 1A to 6A and the comparative example 1A was observed by using the SEM to obtain a macrophotograph at 2000 magnification. The average grain sizes and the average aspect ratios were found as for the first crystal grains and the second crystal grains by using the macrophotograph. Besides, the ratio of the second crystal grains whose long axes were aligned in the length direction was found in the metallic cylinder. Results thereof are illustrated in Table 2 and Table 3.

TABLE 2

|  | First Crystal Grains | |
|---|---|---|
|  | Average Grain Size (µm) | Average Aspect Ratio |
| Example 1A | 67 | 1.3 |
| Example 2A | 96 | 1.5 |
| Example 3A | 155 | 1.7 |
| Example 4A | 195 | 1.8 |
| Example 5A | 160 | 1.7 |
| Example 6A | 170 | 1.8 |
| Comparative Example 1A | 550 | 2.9 |

TABLE 3

|  | Second Crystal Grains | | |
|---|---|---|---|
|  | Average Grain Size (µm) | Average Aspect Ratio | Ratio of Second Crystal Grains Whose Long Axes are Aligned In Length Direction (%) |
| Example 1A | 53 | 2.4 | 85 |
| Example 2A | 128 | 2.8 | 90 |
| Example 3A | 162 | 3.3 | 93 |
| Example 4A | 237 | 3.7 | 100 |
| Example 5A | 185 | 5.5 | 100 |
| Example 6A | 203 | 6.5 | 100 |
| Comparative Example 1A | 25 | 1.6 | 60 |

As it can be seen from Table 2, all of the average aspect ratios of the metallic discs according to the example 1A to the example 6A were less than 2. This is because the working ratio was adjusted to be in the predetermined range. On the other hand, the average aspect ratio of the metallic disc according to the comparative example 1 was 2 or more.

As it can be seen from Table 3, the average aspect ratios were 2 or more in the metallic cylinders whose working ratios were high such as the example 1A to the example 6A. As the working ratio became high, the ratio of the second crystal grains whose long axes were aligned in the length direction became high.

Examples 1B to 6B, Comparative Example 1B

X-ray tubes according to an example 1B to an example 6B and a comparative example 1B were manufactured by using the rotatable anode targets according to the example 1A to the example 6A and the comparative example 1A. When the X-ray tube was manufactured, the dynamic pressure bearing structure was applied as the rotation mechanism. Besides, the liquid-metal lubricant was filled between the inner surface of the metallic cylinder and the fixed shaft.

An exposure test where the electron beam is collided with the X-ray irradiator was performed for each of the X-ray tubes according to the example 1B to the example 6B and the comparative example 1B. After the exposure tests for 10000 cycles were performed, an inside diameter size of the metallic cylinder was measured to measure a deformation amount (µm) before the test and after the test. Results thereof are illustrated in Table 4.

TABLE 4

| X-Ray Tube | Rotatable Anode Target | Deformation Amount Of Metallic Cylinder (µm) |
|---|---|---|
| Example 1B | Example 1A | 10 |
| Example 2B | Example 2A | 7 |
| Example 3B | Example 3A | 4 |
| Example 4B | Example 4A | 3 |
| Example 5B | Example 5A | 3 |
| Example 6B | Example 6A | 3 |
| Comparative Example 1B | Comparative Example 1A | 27 |

As it can be seen from Table 4, a change amount of the metallic cylinder was small in each of the X-ray tubes according to the example 1B to the example 6B. It turns out from the above that long-term reliability of each of the X-ray tubes according to the example 1B to the example 6B is excellent. The structure with good heat release performance and where the thermal deformation is difficult to occur enables the above. As a result, it is possible to continuously operate the X-ray inspection apparatus using the X-ray tube according to the embodiment.

Examples 7A to 10A

The molybdenum (Mo) powder whose average grain size was 3 µm and a TiC powder whose average grain size was 1 µm were prepared as the raw material powder constituting the metallic disc. A mixed raw material powder containing the TiC powder with 0.8 weight % and the Mo powder of the remaining part was prepared.

The mixed raw material powder was molded by the mold, and a disc-shaped compact including the hole to be joined with the metallic cylinder was prepared. Next, the sintering process was performed at 2000° C. or more and 2200° C. or less in vacuum ($10^{-3}$ Pa or less). The forging was performed for the obtained Mo alloy sintered compact at the working ratio illustrated in Table 5. The working ratio is a working ratio in the thickness direction of the metallic disc.

The surface polishing was performed for the obtained Mo alloy forged compact. The X-ray irradiator made up of the Re—W alloy layer was provided at the surface of the metallic disc. The $TiO_2$—$Al_2O_3$ film (film thickness of 40 μm) was provided at the surface of the metallic disc where the X-ray irradiator was not provided.

The molybdenum (Mo) powder whose average grain size was 5 μm was prepared as the raw material powder constituting the metallic cylinder. Next, the sintering process was performed at 2000° C. or more and 2200° C. or less in vacuum ($10^{-3}$ Pa or less). Then the rolling and the forging were performed for the obtained Mo sintered compact at the working ratio illustrated in Table 5 to prepare the plate-state member. The above-stated working ratio is a working ratio in a length direction of the metallic cylinder.

Sizes of the obtained metallic discs and the metallic cylinders are illustrated in Table 5 and Table 6. Besides, the surface polishing was performed for the surface of the metallic disc to be joined with the metallic cylinder and the surface of the metallic cylinder to be joined with the metallic disc with the surface roughness of Ra 3 μm or less.

Next, as illustrated in Table 6, the metallic disc and the metallic cylinder were joined by using the Ti brazing material (melting point of 1600° C.) or the Zr brazing material (melting point of 1550° C.). Rotatable anode targets according to the example 7A to the example 10A were manufactured by the above-stated processes.

TABLE 5

| | Metallic Disc | | |
| --- | --- | --- | --- |
| | Working Ratio (%) | Diameter (mm) × Thickness (mm) | Diameter of Hole (mm) |
| Example 7A | 35 | 200 × 60 | 70 |
| Example 8A | 40 | 160 × 50 | 50 |
| Example 9A | 45 | 120 × 40 | 40 |
| Example 10A | 45 | 100 × 30 | 40 |

TABLE 6

| | Metallic Cylinder | | |
| --- | --- | --- | --- |
| | Working Ratio (%) | Outside Diameter (mm) × Inside Diameter (mm) × Length (mm) | Brazing Material |
| Example 7A | 35 | 70 × 60 × 120 | Ti Brazing Material |
| Example 8A | 30 | 50 × 40 × 100 | Ti Brazing Material |
| Example 9A | 25 | 40 × 30 × 100 | Zr Brazing Material |
| Example 10A | 20 | 40 × 30 × 80 | Zr Brazing Material |

A sectional structure of the rotatable anode target including a region within 2 mm from the interface between the metallic disc and the metallic cylinder of each of the X-ray tube anode targets according to the example 7A to the example 10A was observed by using the SEM to obtain the macrophotograph at 2000 magnification. The average grain sizes and the average aspect ratios were found as for the first crystal grains and the second crystal grains by using the macrophotograph. Besides, the ratio of the second crystal grains whose long axes were aligned in the length direction was found in the metallic cylinder. Results thereof are illustrated in Table 7 and Table 8.

As it can be seen from Table 7, all of the average aspect ratios of the metallic discs according to the example 7A to the example 10A were less than 2. This is because the working ratio was adjusted to be in the predetermined range.

As it can be seen from Table 6, Table 8, the average aspect ratio was 2 or more in the metallic cylinder whose working ratio was high such as the example 7A to the example 10A. The working ratio was adjusted in the predetermined range, and thereby, the ratio of the second crystal grains whose long axes were aligned in the length direction became high.

TABLE 7

| | First Crystal Grains | |
| --- | --- | --- |
| | Average Grain Size (μm) | Average Aspect Ratio |
| Example 7A | 340 | 1.7 |
| Example 8A | 292 | 1.5 |
| Example 9A | 223 | 1.4 |
| Example 10A | 195 | 1.3 |

TABLE 8

| | Second Crystal Grains | | |
| --- | --- | --- | --- |
| | Average Grain Size (μm) | Average Aspect Ratio | Ratio of Second Crystal Grains Whose Long Axes are Aligned In Length Direction (%) |
| Example 7A | 452 | 3.9 | 100 |
| Example 8A | 308 | 3.6 | 100 |
| Example 9A | 255 | 3.2 | 98 |
| Example 10A | 231 | 2.9 | 96 |

Examples 7B to 10B

X-ray tubes were manufactured by using the rotatable anode targets according to the example 7A to the example 10A. When the X-ray tube was manufactured, the dynamic pressure bearing structure was applied as the rotation mechanism. The liquid-metal lubricant was filled between the inner surface of the metallic cylinder and the fixed shaft. The exposure test where the electron beam was collided with the X-ray irradiator was performed for each of the X-ray tubes according to the example 7B to the example 10B. After the exposure tests for 10000 cycles were performed, an inside diameter size of each metallic cylinder was measured to measure a deformation amount (μm) before the test and after the test. Results thereof are illustrated in Table 9.

TABLE 9

| X-Ray Tube | Rotatable Anode Target | Deformation Amount of Metallic Cylinder (μm) |
| --- | --- | --- |
| Example 7B | Example 7A | 5 |
| Example 8B | Example 8A | 4 |
| Example 9B | Example 9A | 7 |
| Example 10B | Example 10A | 7 |

It can be seen from Table 9 that the change amount was small even when the Mo alloy was used and the sizes of the metallic disc and the metallic cylinder were changed. It turns out that the rotatable anode target has high heat release performance and has a structure where the thermal deformation is difficult to occur.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. These embodiments and the modification examples thereof would fall within the scope and spirit of the invention, and would be fall within the invention described in the claims and the range equivalent thereto. Further, each embodiment described above can be implemented in combination with each other.

What is claimed is:

1. A method of manufacturing a rotatable anode target for an X-ray tube, comprising:
    molding a first raw material powder containing at least one metal selected from the group consisting of molybdenum, tungsten, tantalum, niobium, and iron, or an alloy containing the at least one metal to form a first compact, sintering the first compact to form a sintered compact, and processing the sintered compact into a disc shape to form a metallic disc;
    forming an X-ray irradiator on the disc;
    molding a second raw material powder containing at least one metal selected from the group consisting of molybdenum, tungsten, tantalum, niobium, and iron, or an alloy containing the at least one metal of the second raw material powder to form a second compact and processing the second compact into a cylindrical shape to form a metallic cylinder; and
    joining the disc and the cylinder,
    wherein the disc has a plurality of first crystal grains in a first region within 2 mm from an interface between the disc and the cylinder, and the cylinder has a plurality of second crystal grains in a second region within 2 mm from the interface, and
    wherein a first average aspect ratio of the first crystal grains is 1.3 or more and 1.8 or less, and a second average aspect ratio of the second crystal grains is 2.4 or more and 6.5 or less.

2. The method according to claim 1,
    wherein a directional shift of an axis direction of each of the second crystal grains of 80% or more and 100% or less in number ratio per a unit area of 1000 μm×1000 μm to a length direction of the cylinder is 25 degrees or more and 25 degrees or less.

3. The method according to claim 1,
    wherein an average grain size of the first crystal grains is 20 μm or more and 500 μm or less.

4. The method according to claim 1,
    wherein an average grain size of the second crystal grains is 20 μm or more and 800 μm or less.

5. The method according to claim 1,
    wherein the cylinder is joined with the disc by a brazing material therebetween.

6. The method according to claim 5,
    wherein the brazing material contains at least one element selected from the group consisting of Ti, Zr, Hf, Pt, Co, Cr, Ni, and V.

7. The method according to claim 1, further comprising:
    forming a metal oxide coating film on the disc.

8. The method according to claim 7,
    wherein the film contains a mixture of a titanium oxide and an aluminum oxide.

9. The method according to claim 1, further comprising:
    joining a graphite member to the disc.

10. The method according to claim 1,
    wherein a thickness of the disc is 10 mm or more and 60 mm or less.

11. The method according to claim 1,
    wherein the X-ray irradiator contains an alloy of Re and W.

12. The method according to claim 1, further comprising:
    providing a fixed shaft through the cylinder; and
    applying a liquid-metal lubricant between the cylinder and the fixed shaft.

13. A method of manufacturing an X-ray tube, comprising:
    manufacturing a rotatable anode for an X-ray tube by the method according to claim 1; and
    providing a vacuum vessel which holds the anode and a cathode to irradiate an electron beam on the X-ray irradiator.

14. A method of manufacturing an X-ray inspection apparatus, comprising:
    manufacturing an X-ray tube by the method according to claim 13;
    providing a detector to detect transmitted X-ray; and
    providing an image generator to generate an image corresponding to detected data from the detector.

15. The method according to claim 1,
    wherein a working ratio of the sintered compact by the processing is 10% or more and 60% or less, and
    wherein a working ratio of the second compact by forming the cylinder is 10% or more and 90% or less.

* * * * *